United States Patent [19]

Nieh

[11] Patent Number: 4,767,555
[45] Date of Patent: Aug. 30, 1988

[54] HYDROPHOBIC EPOXIDE MODIFIED POLYOXYALKYLENE DIAMINES AND THICKENED AQUEOUS FLUIDS

[75] Inventor: Edward C. Y. Nieh, Austin, Tex.
[73] Assignee: Texaco Inc., White Plains, N.Y.
[21] Appl. No.: 36,637
[22] Filed: Apr. 10, 1987
[51] Int. Cl.$^4$ .......................................... C10M 173/02
[52] U.S. Cl. .................... 252/73; 252/49.3; 252/75; 252/77; 524/608; 528/121; 528/405; 528/422; 564/316; 564/348; 564/475
[58] Field of Search ............ 252/49.3, 75, 77, 73; 524/608; 528/121, 405, 422; 564/316, 348, 475

[56] References Cited
U.S. PATENT DOCUMENTS

| | | | |
|---|---|---|---|
| 2,792,367 | 5/1957 | De Groote et al. | 564/348 |
| 4,390,440 | 6/1983 | Schwartz et al. | 252/78.5 |
| 4,396,499 | 8/1983 | McCoy et al. | 210/708 |
| 4,606,837 | 8/1986 | McEntire et al. | 252/75 |

Primary Examiner—Robert Wax
Attorney, Agent, or Firm—Jack H. Park; Kenneth R. Priem; Richard A. Morgan

[57] ABSTRACT

Aqueous fluids are thickened with epoxide modified polyoxyalkylene diamines. The polyoxyalkylene diamines are of the formula:

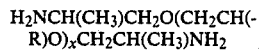

$$H_2NCH(CH_3)CH_2O(CH_2CH(R)O)_xCH_2CH(CH_3)NH_2$$

wherein:
R is methyl or hydrogen and
x is a number selected to give the diamine a molecular weight of 3000 to 9000.

The epoxide is a hydrophobic monoepoxide, diepoxide or mixture thereof.

The aqueous fluid optionally incorporate ethylene glycol. They are useful for water/glycol base hydraulic fluids, cosmetics and surfactants.

9 Claims, No Drawings

HYDROPHOBIC EPOXIDE MODIFIED POLYOXYALKYLENE DIAMINES AND THICKENED AQUEOUS FLUIDS

BACKGROUND OF THE INVENTION

1. Field of the Invention

The invention relates to epoxide modified polyoxyalkylene diamine mixtures and thickened aqueous fluids therefrom. More specifically, the invention relates to aqueous fluids thickened with a selected 3000 to 9000 molecular weight polyoxyalkylene diamine reacted with a hydrophobic epoxide.

The thickened fluids are useful for water/glycol based hydraulic fluids, cosmetics and surfactant solutions.

2. Other Thickeners in the Field

U.S. Pat. No. 4,396,499 to McCoy et al. discloses water-soluble salts of polymers prepared by the reaction of polyoxyalkylene diamines and diepoxides. The diamines are of the formula: $H_2NCH(CH_3)CH_2O(CH_2CH(R)O)_xCH_2CH(CH_3)NH_2$.

U.S. Pat. No. 4,606,837 to McEntire et al. discloses water-glycol fluids made from polyoxyalkylene thickeners. These thickeners are prepared by the reaction of ethylene oxide with a 10 to 50 carbon atom hydrophobe such as dinonylphenol in a specified ratio.

U.S. Pat. Nos. 4,310,436 and 4,354,956 to Camp disclose polyethylene glycol fatty acid diesters used as thickening agents. U.S. Pat. No. 4,395,351 to Camp discloses ethylene oxide adducts of coconut fatty acid amine, coco fatty acid and oleic acid for use as thickeners.

U.S. Pat. No. 4,390,440 to Schwartz et al. discloses a carboxylic acid having 5 to 20 carbon atoms, a thickener which is a polyether polyol of molecular weight of 1000 to 40,000 prepared by reacting ethylene oxide with at least one active hydrogen-containing compound and at least one alpha-olefin oxide or alcohol or glycidyl ether.

U.S. Pat. No. 3,992,312 to Genjida et al. discloses thickeners comprising a water-soluble polymer. The polymer contains a polyamide residue bonded to an oxyalkylene chain. Suitable polyamides include the condensation product of a polycarboxylic acid and a polyamine. Examples of polycarboxylic acids include adipic acid and polymerized fatty acids (dimer acids). Suitable polyamines include aliphatic polyamines such as ethylene diamine, propylene diamine and butylene diamine.

SUMMARY OF THE INVENTION

The invention concerns water based fluids comprising an effective amount of a thickener. The thickener is the reaction product of a polyoxyalkylene diamine and a hydrophobic monoepoxide, diepoxide or mixture thereof. The diamine is of the formula:

$H_2NCH(CH_3)CH_2O(CH_2CH(R)O)_xCH_2CH(CH_3)NH_2$.

About 1% to 30% of R is methyl with the balance being hydrogen. The number x is a value that specifies the molecular weight of the polyoxyalkylene diamine in the range of 3000 to 9000. The hydrophobic epoxide is a monoepoxide, diepoxide or mixture thereof. The ratio of amine equivalent: monoepoxide ranges from 1:1 to 1:1.9 and the ratio of amine equivalent: diepoxide ranges from 1:0.08 to 1:0.12.

DESCRIPTION OF THE PREFERRED EMBODIMENTS

The thickeners of the invention are useful for thickening water or an aqueous solution of organic solvents. These thickeners have a relatively low molecular weight for their effectiveness in thickening. Low molecular weight thickeners are more stable to shear degradation than high molecular weight thickeners. This makes them useful for thickening water and water/glycol based hydraulic fluids where resistance to thinning with use is an important consideration.

A variety of monoepoxides are useful for the instant thickeners. Among these are the epoxides of 8 to 22 carbon number alpha olefin oxides and 8 to 22 carbon number alkyl glycidyl ethers. Particularly preferred are the epoxides of 8 to 14 carbon number alpha olefin oxides and 8 to 14 carbon number alkyl glycidyl ethers.

A variety of diepoxides are useful for the instant thickeners. These include the diglycidyl ethers of 4,4'-isopropylidenediphenol (bisphenol A); 4,4-isopropylidenebis (2,6-dibromophenol) (tetrabomo bisphenol A); resorcinol; neopentylglycol; 1,4-butanediol and poly(oxypropylene)glycol. The diglycidyl ethers of bisphenol A, resorcinol and 1,4-butanediol are preferred. These diepoxides are prepared by the reaction of epichlorohydrin with a hydroxyl compound.

Other useful diepoxides prepared by epoxidation with peracetic acid include vinylcyclohexene dioxide;
3,4-epoxycyclohexylmethyl 3,4-epoxycyclohexane carboxylate;
3-(3,4-epoxycyclohexane)-8,9-epoxy-2,4-dioxaspiro[5,5]-undecane;
bis(2,3-epoxycyclopentyl)ether and
bis(3,4-epoxy-6-methylcyclohexylmethyl)adipate.

Diamines used to formulate the thickeners of the invention are commercially available as Jeffamine ® ED-6075, ED-6000 and ED-4000. The amine function gives the thickener reserve alkalinity and provides rust inhibition.

The thickener formulations are prepared by stirring the constituents in a stainless steel kettle at 60° C. to 100° C. The blends are then diluted with the desired amount of water or organic solvent to make the concentrate. The fluids are shipped as concentrates. Before use they are diluted with water and optionally ethylene glycol, typically 1 wt % to 30 wt % concentrate in water.

This invention is shown by way of example.

EXAMPLE

Jeffamine ® ED-6075 is a 5400 molecular weight polyoxyalkylene diamine product made by Ni/Cu/Cr catalyzed reductive amination of a corresponding polyoxyalkylene diol consisting of 75% of oxyethylene units and 22% of oxypropylene units ramdomly distributed in the main segment and 3% oxypropylene units at the end of the polymer chain. The reductive amination was conducted in a 1.5 liter tubular reactor filled with 1.2 liter of Ni/Cu/Cr catalyst (described in U.S. Pat. No. 3,654,370 to Yeakey, incorporated herein by reference) maintained at 204° C. and 2000 psia pressure. The polyoxyalkylene diol, ammonia and hydrogen were fed to the reactor at respective rates of 0.43 lb/hr., 1.04 lb/hr. and 35 liter/hr. The reactor effluent was collected for the last 23 hour period of the 26 hour period. The effluent was stripped of volatiles and analyzed as followed: 0.37 meq/g total acetylable, 0.30 meq/g total amines, 0.28 meq/g primary amines and 0.05 wt % water. The melting point of this product was 30° C.

Jeffamine® ED-6000 is a 6350 molecular weight polyoxyalkylene diamine product made by Ni/Cu/Cr catalyzed reductive amination of a corresponding polyoxyalkylene diol consisting of mostly oxyethylene units and 3.5% of oxypropylene units at the end of the polymer chain. The reductive amination reaction was conducted in a similar manner as for ED-6075. The stripped product analyzed as followed: 0.315 meq/g total acetylable, 0.27 meq/g total amine, 0.25 meq/g primary amines and 0.05 wt % water. The melting point of the product was 57° C.

Jeffamine® ED-4000 is a 3846 molecular weight polyoxyalkylene diamine product made by Ni/Cu/Cr catalyzed reductive amination of a corresponding polyoxyalkylene diol consisting of mostly oxyethylene units and 3.5% of oxypropylene units at the end of the polymer chain. The reductive amination reaction was conducted in a similar manner as for ED-6075. The stripped product was analyzed as followed: 0.52 meq/g total acetylable, 0.45 meq/g total amine, 0.43 meq/g primary amine and 0.23% water. The melting point of the product was 54° C.

EXAMPLE I

General Synthesis

Quantities of polyoxyalkylene diamine and n-alkyl glycidyl ether were admixed in a glass vial at 60° C. and then heated to 115° C. for a period of 20 hours. No catalyst was used. However an acid or base catalyst is appropriate for some reagents. The completion of the addition of amine to epoxide was indicated when a 10% aqueous solution of the resulting product was clear at temperatures below the cloud point of the product. The results of these reactions are summarized in Table I.

Heloxy® WC-7 is a mixture of $C_8$ and $C_{10}$ linear alkyl glycidyl ethers, 3.92 meq/g epoxide. Heloxy® WC-8 is a mixture of $C_{12}$ and $C_{14}$ linear alkyl glycidyl ethers, 3.13 meq/g epoxide. Both are a product of Wilmington Chemical Co.

TABLE I

| Example | Jeffamine® Diamine | Amount (gram) | Epoxide | Amount (gram) | Viscosity cs @ 100° F. 10% in water | (a.) Vis cs @ 40° C. % in aqueous ethylene glycol 10% | 15% | 20% | (b.) Wt % Required for 40 cs Vis @ 40° C. |
|---|---|---|---|---|---|---|---|---|---|
| I-1. | ED-6000 | | None | | 2.5 cs | | | | |
| 2. | ED-6075 | | None | | 2.5 | | | | |
| 3. | ED-4000 | | None | | | | | | |
| 4. | ED-6000 | 40.0 | Heloxy® WC-7 | 4.50 | 12.7 | 14.6 cs | 79.4 cs | 180 cs | 12.0 wt % |
| 5. | ED-6000 | 40.0 | Heloxy® WC-7 | 2.25 | 32.0 | 34.0 | 191 | 492 | 10.5 |
| | | | Heloxy® WC-8 | 2.25 | | | | | |
| 6. | ED-6000 | 40.0 | Heloxy® WC-8 | 4.50 | 126 | 52.0 | 278 | 840 | 9.5 |
| 7. | ED-6000 | 40.0 | Heloxy® WC-7 | 4.80 | 197 | 42.9 | 174 | 447 | 10.0 |
| 8. | ED-6000 | 40.0 | Heloxy® WC-7 | 2.40 | 182 | 38.0 | 215 | 609 | 10.0 |
| | | | Heloxy® WC-8 | 2.40 | | | | | |
| 9. | ED-6000 | 40.0 | Heloxy® WC-8 | 4.80 | Jelly | 435 | 5636 | 19837 | 5.5 |
| 10. | ED-6075 | 50.0 | Heloxy® WC-7 | 6.00 | 9.7 | 14.0 | 40.2 | 134 | 15.0 |
| 11. | ED-6075 | 50.0 | Heloxy® WC-7 | 3.00 | 19.3 | 31.2 | 69.4 | 227 | 11.5 |
| | | | Heloxy® WC-7 | 3.00 | | | | | |
| 12. | ED-6075 | 50.0 | Heloxy® WC-8 | 6.00 | 58.4 | 36.5 | 141 | 396 | 10.5 |
| 13. | ED-6075 | 44.0 | Heloxy® WC-7 | 6.00 | 139 | 33.5 | 170 | 576 | 10.5 |
| 14. | ED-6075 | 44.0 | Heloxy® WC-7 | 3.00 | | | | | |
| 15. | | | Heloxy® WC-8 | 3.00 | 296 | 60.5 | 641 | 2003 | 9.5 |
| 16. | ED-6075 | 44.0 | Heloxy® WC-8 | 6.00 | 55.6 | 88.5 | 875 | 3611 | 8.5 |
| 17. | ED-4000 | 40.0 | Heloxy® WC-8 | 7.13 | 50.0 | 54.0 | 352 | 1809 | 9.0 |
| 18. | ED-4000 | 40.0 | Heloxy® WC-7 | 7.13 | 64.0 | 24.0 | 96 | 360 | 11.7 |

(a.) Solution in 1:1 w/w ethylene glycol/water
(b.) Solution in 1:1 w/w ethylene glycol/water formulated for a fire resistant hydraulic fluid.

EXAMPLE II

General Synthesis

Quantities of polyoxyalkylene diamine, n-alkyl glycidyl ether and diglycidyl ether were admixed in a glass vial at 60° C. and then heated to 115° C. for a period of 20 hours. No catalyst was used. However an acid or base catalyst is appropriate for some reagents. The completion of the addition of amine to epoxide was indicated when a 10% aqueous solution of the resulting product was clear at temperatures below the cloud point of the product. The results of these reactions are summarized in Table II.

Epon® 828 is the diglycidyl ether of bisphenol A, 5.26 meq/g. It is a product of Shell Chemical Co.

Heloxy® WC-67 is the diglycidyl ether of 1,4-butanediol, 8.11 meq/g epoxide. Heloxy® WC-68 is the diglycidyl ether of neopenty glycol, 7.46 meq/g epoxide. Both are a product of Wilmington Chemical Co.

TABLE II

| Example | Jeffamine® Diamine | Amount (gram) | Diepoxide | Amount (gram) | Viscosity cs @ 100° F. 10% in water | (a.) Vis cs @ 40° C., % in aqueous ethylene glycol 10% | 15% | 20% | (b.) Wt % Required For 40 cs Vis @ 40° C. |
|---|---|---|---|---|---|---|---|---|---|
| II-1. | ED-6000 | | None | | 2.5 | | | | |
| 2. | ED-6075 | | None | | 2.5 | | | | |
| 3 | ED-4000 | | None | | 2.4 | | | | |
| 4. | ED-6000 | 23.1 | Epon® 828 | 0.9 | 5.0 | 12.4 cs | 26.5 cs | 49.6 cs | 17.2 wt % |
| 5. | ED-6000 | 22.8 | Epon® 828 | 1.2 | 4.9 | 20.0 | 59.9 | 130 | 14.4 |
| 6. | ED-6000 | 22.5 | Epon® 828 | 1.5 | Jelled | *6%-32.6 | | | 6.7 |

TABLE II-continued

| Example | Jeffamine ® Diamine | Amount (gram) | Diepoxide | Amount (gram) | Viscosity cs @ 100° F. 10% in water | (a.) Vis cs @ 40° C., % in aqueous ethylene glycol | | | (b.) Wt % Required For 40 cs Vis @ 40° C. |
|---|---|---|---|---|---|---|---|---|---|
| | | | | | | 10% | 15% | 20% | |
| | | | | | *8%-187.1 | | | | |
| 7. | ED-6000 | 40.0 | Heloxy ® WC-67 | 4.2 | 4.35 | 12.8 | 24.7 | 48.6 | 19.0 |
| 8. | ED-6000 | 40.0 | Heloxy ® WC-67 | 4.6 | 3.20 | 9.3 | 40.1 | 79.6 | 15.0 |
| 9. | ED-6000 | 40.0 | Heloxy ® WC-68 | 4.2 | 3.50 | 9.8 | 17.8 | 29.5 | 24.5 |
| 10. | ED-6000 | 40.0 | Heloxy ® WC-68 | 5.0 | 4.38 | 12.7 | 24.4 | 46.8 | 17.5 |
| 11. | ED-6075 | 38.0 | Epon ® 828 | 2.0 | 12.3 | 20.1 | 40.6 | 106 | 14.2 |
| 12. | ED-6075 | 37.5 | Epon ® 828 | 2.2 | 23.4 | 27.2 | 64.7 | 166 | 12.5 |
| 13. | ED-6075 | 37.6 | Epon ® 828 | 2.4 | 59.2 | 43.5 | 139 | 276 | 9.5 |
| 14. | ED-6075 | 37.4 | Epon ® 828 | 2.6 | 276 | 89 | 400 | 1347 | 7.0 |
| 15. | ED-4000 | 40.0 | Epon ® 828 | 2.5 | 4.6 | 10.6 | 22.5 | 40.8 | 20.0 |
| 16. | ED-4000 | 40.0 | Epon ® 828 | 2.8 | .34 | 16.8 | 37.7 | 80.5 | 15.5 |
| 17. | ED-4000 | 40.0 | Epon ® 828 | 3.1 | 10.9 | 20.4 | 48.4 | 103 | 14.0 |
| 18. | ED-6075 | 40.0 | Heloxy ® WC-68 | 5.0 | 4.6 | 11.3 | 26.3 | 52.9 | 19.0 |
| 19. | ED-6075 | 40.0 | Heloxy ® WC-67 | 4.5 | 6.0 | 32.8 | 71.9 | 161.0 | 12.0 |

(a.) Solution in 1:1 w/w ethylene glycol/water
(b.) Solution in 1:1 w/w ethylene glycol/water formulated for a fire resistant hydraulic fluid.
*Vis cs @ 40° F., 6% and 8% in aqueous ethylene glycol.

EXAMPLE III

General Synthesis

Quantities of polyoxyalkylene diamine, n-alkyl glycidyl ether and diglycidyl ether were admixed in a glass vial at 60° C. and then heated to 115° C. for a period of 20 hours. No catalyst was used. However an acid or base catalyst is appropriate for some reagents. The completion of the addition of amine to epoxide was indicated when a 10% aqueous solution of the resulting product was clear at temperatures below the cloud point of the product. The results of these reactions are summarized in Table III.

TABLE III

| Example | Jeffamine ® Diamine | Amount (gram) | Epoxide | Amount (gram) | Viscosity cs @ 100° F. 10% in water | (a.) Vis cs @ 40° C., % in aqueous ethylene glycol | | | (b.) Wt % Required For 40 cs Vis @ 40° C. |
|---|---|---|---|---|---|---|---|---|---|
| | | | | | | 10% | 15% | 20% | |
| III-1. | ED-6000 | | None | | 2.4 cs | | | | |
| 2. | ED-6075 | | None | | 2.5 | | | | |
| 3. | ED-4000 | | None | | 2.4 | | | | |
| 4. | ED-6000 | 40.0 | Heloxy ® WC-7 Epon ® 828 | 2.25 1.05 | 16.6 | 15.5 cs | 46.9 cs | 96.7 cs | 14.5 wt % |
| 5. | ED-6000 | 40.0 | Heloxy ® WC-7 Heloxy ® WC-8 Epon ® 828 | 1.05 1.05 1.05 | 25.3 | 21.7 | 64.5 | 159 | 12.2 |
| 6. | ED-6000 | 40.0 | Heloxy ® WC-8 Epon ® 828 | 2.25 1.05 | 45.6 | 7.3 | 41.8 | 214.6 | 15.0 |
| 7. | ED-6000 | 50.0 | Heloxy ® WC-7 Epon ® 828 | 3.30 1.65 | 98.4 | 32.0 | 131 | 412 | 10.7 |
| 8. | ED-6000 | 50.0 | Heloxy ® WC-7 Heloxy ® WC-8 Epon ® 828 | 1.65 1.65 1.65 | 849 | 122 | 957 | 29.0 | 7.5 |
| 9. | ED-6000 | 50.0 | Heloxy ® WC-8 Epon ® 828 | 3.30 1.65 | 4174 | 142 | 1040 | 38.1 | 7.5 |
| 10. | ED-6075 | 50.0 | Heloxy ® WC-7 Epon ® 828 | 3.80 1.65 | 82 | 29.0 | 85.7 | 208 | 9.5 |
| 11. | ED-6075 | 50.0 | Heloxy ® WC-7 Heloxy ® WC-8 Epon ® 828 | 1.65 1.65 | 258 | 52 | 244 | 594 | 9.0 |
| 12. | ED-6075 | 50.0 | Heloxy ® WC-8 Epon ® 828 | 3.30 1.65 | 232 | 45.3 | 252 | 743 | 11.5 |
| 13. | ED-6000 | 50.0 | Heloxy ® WC-7 Heloxy ® WC-8 | 1.05 3.30 | 43.5 | 28.9 | 104 | 215 | 12.8 |
| 14. | ED-6000 | 50.0 | Heloxy ® WC-68 Heloxy ® WC-8 | 1.15 3.30 | 60.6 | 34.2 | 132 | 308 | 10.5 |
| 15. | ED-6075 | 50.0 | Heloxy ® WC-67 Heloxy ® WC-8 | 1.05 3.30 | 39.1 | 26.5 | 63.9 | 312 | 12.5 |
| 16. | ED-6075 | 50.0 | Heloxy ® WC-68 Heloxy ® WC-8 | 1.10 3.30 | 38.4 | 35.2 | 146 | 679 | 10.5 |
| 17. | ED-4000 | 40.0 | Heloxy ® WC-8 Epon ® 828 | 5.8 1.0 | Jelly | 899 | 15380 | 3688 | 5.5 |
| 18. | ED-4000 | 40.0 | Heloxy ® WC-7 Epon ® 828 | 5.8 1.9 | 75 | 63 | 332 | 875 | 8.5 |
| 19. | ED-6075 | 50.0 | Heloxy ® WC-8 Heloxy ® WC-68 | 3.35 1.20 | 46.6 | 35.9 | 128 | 393 | 10.5 |
| 20. | ED-6075 | 50.0 | Heloxy ® WC-8 Heloxy ® WC-68 | 3.30 1.40 | 35.2 | 37.4 | 197 | 727 | 10.5 | a. Solution in 1:1 w/w ethylene glycol/water
b. Solution in 1:1 w/w ethylene glycol/water formulated for a fire resistant hydraulic fluid.

While particular embodiments of the invention have been described, it is well understood that the invention is not limited thereto since modifications may be made. It is therefore contemplated to cover by the appended claims any such modifications as fall within the spirit and scope of the claims.

What is claimed is:

1. An aqueous fluid comprising an effective thickening amount of a thickener comprising the reaction product of:
   a. a polyoxyalkylene diamine of the formula:

$$H_2NCH(CH_3)CH_2O(CH_2CH(R)O)_xCH_2CH(CH_3)NH_2$$

wherein: from 1% to 30% of R is methyl and the remaining R is hydrogen, and x is a number such that the molecular weight of the polyoxyalkylene diamine ranges from 3000 to 9000; with
   b. a mixture of a hydrophobic monoepoxide comprising a $C_8$ to $C_{22}$ alpha olefin of alkyl glycidyl ether and a hydrophobic diepoxide
   wherein: the ratio amine equivalent: monoepoxide: diepoxide in the range of 1:0.25:0.25 to 1:1.4:1.

2. The aqueous fluid of claim 1 wherein the monoepoxide is a $C_8$ to $C_{14}$ alpha olefin or alkyl glycidyl ether.

3. The aqueous fluid of claim 1 wherein the amount of thickener is from 1 wt % to 30 wt %.

4. The aqueous fluid of claim 1 wherein the aqueous fluid additional comprises ethylene glycol.

5. An aqueous fluid comprising the reaction product of:
   a. a polyoxyalkylene diamine of the formula:

$$H_2NCH(CH_3)CH_2O(CH_2CH(R)O)_xCH_2CH(CH_3)NH_2$$

wherein: from 1% to 30% of R is methyl and the remaining R is hydrogen, and x is a number such that the molecular weight of the polyoxyalkylene diamine ranges from 3000 to 9000; with
   b. a hydrophobic monoepoxide comprising a $C_8$ to $C_{22}$ alpha olefin or alkyl glycidyl ether
   wherein: the ratio amine equivalent: epoxide is in the range of 1:1 to 1:1.9.

6. The composition of claim 5 wherein the hydrophobic monoepoxide is a $C_8$ to $C_{14}$ alpha olefin glycidyl ether.

7. The composition of claim 5 wherein the hydrophobic monoepoxide is a $C_8$ to $C_{14}$ alkyl glycidyl ether.

8. The aqueous fluid of claim 5 wherein the amount of thickener is from 1 wt % to 30 wt %.

9. The aqueous fluid of claim 5 which additionally comprises ethylene glycol.

* * * * *